(12) United States Patent
Amr et al.

(10) Patent No.: US 9,896,476 B1
(45) Date of Patent: Feb. 20, 2018

(54) GLYCYRRHETIC ACID DERIVATIVES

(71) Applicant: KING SAUD UNIVERSITY, Riyadh (SA)

(72) Inventors: Abd El-Galil E. Amr, Riyadh (SA); Mohamed A. Al-Omar, Riyadh (SA); Nagy Mahmoud Hassan Khalifa, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/711,926

(22) Filed: Sep. 21, 2017

(51) Int. Cl.
*C07J 63/00* (2006.01)
*A61K 31/415* (2006.01)

(52) U.S. Cl.
CPC .......... *C07J 63/008* (2013.01); *A61K 31/415* (2013.01)

(58) Field of Classification Search
CPC ....................................................... C07J 63/008
USPC ......................................................... 514/406
See application file for complete search history.

(56) References Cited

U.S. PATENT DOCUMENTS

| | | | |
|---|---|---|---|
| 4,395,423 | A | 7/1983 | Neumann |
| 7,790,759 | B2 | 9/2010 | Wang et al. |
| 8,324,264 | B1 | 12/2012 | Eldridge et al. |
| 9,593,074 | B2 | 3/2017 | Bender et al. |
| 2009/0062401 | A1 | 3/2009 | Odermatt et al. |

FOREIGN PATENT DOCUMENTS

| | | |
|---|---|---|
| EP | 0009801 A1 | 4/1980 |
| JP | 6183145 A | 4/1986 |

OTHER PUBLICATIONS

Roshan, Asha et al., Phytochemical Constituent, Pharmacological Activities and Medicinal uses through the Millenia of Glycyrrhiza Glabra Linn: A Review; IRJP, 2012, 45-55, 3(8).
Song, Heng et al., Synthesis and Biological Evaluation of Novel Hydrogen Sulfide Releasing Glycyrrhetic Acid Derivatives; Journal of Enzyme Inhibition and Medicinal Chemistry; 2016, 1457-1463, 31(6).
Verma, M. et al., Antiinflammatory Activity of Novel Indole Derivatives; Eur.JMed.Chem., 1994, 941-946, 29.
Bekhit, A. et al., Design and Synthesis of some Substituted 1 H Pyrazolyl oxazolidines or 1H Pyrazolyl thiazolidines as Anti-inflammatory antimicrobial agents; 2003, 111-118, 2.

Primary Examiner — Kristin Vajda
(74) Attorney, Agent, or Firm — Richard C. Litman (57) ABSTRACT

The glycyrrhetic acid derivatives can include:

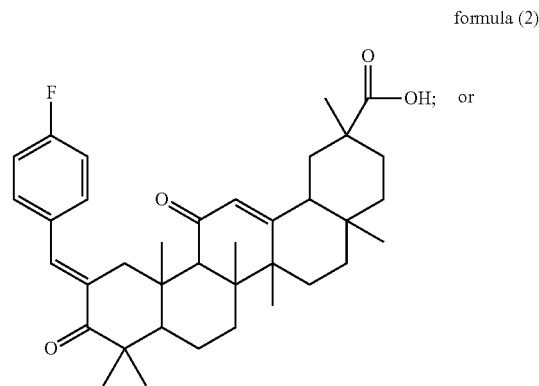

formula (2)

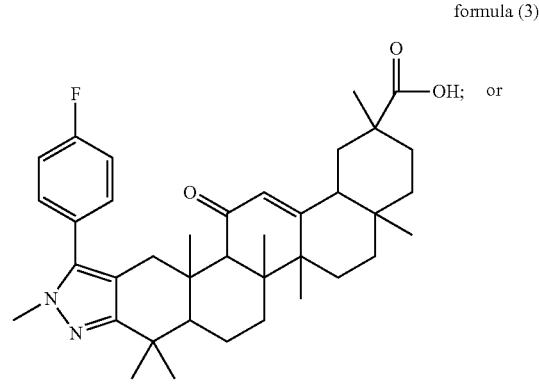

formula (3)

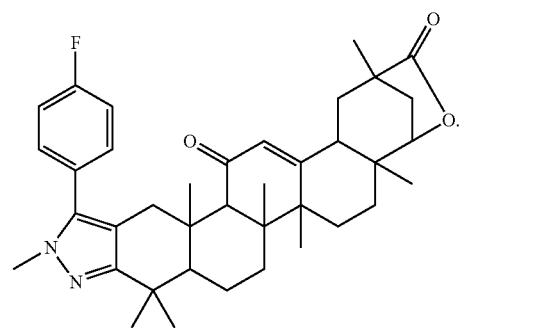

formula (4)

The glycyrrhetic acid derivatives can be used to treat inflammation and/or ulcers.

15 Claims, 3 Drawing Sheets

GLYCYRRHETIC ACID DERIVATIVES

BACKGROUND OF THE INVENTION

1. Field

The disclosure of the present patent application relates to glycyrrhetic acid derivatives, and particularly to glycyrrhetic acid derivatives as anti-inflammatory and antiulcer agents.

2. Description of the Related Art

Glycyrrhetic acid is a pentacyclic triterpenoid derivative obtained by acid hydrolysis of glycyrrhizic acid, which is found in liquorice. Glycyrrhetic acid has antiulcerogenic activity, and so is used in the treatment of peptic ulcers. In addition, glycyrrhetic acid exhibits some additional pharmacological properties including anticancer activity, immune-modulator activity, and hepatoprotective activity. Chemical alterations of glycyrrhetic acid have led to the formation of phenolic esters, anilides and ureides having potent anti-inflammatory activities.

The structure of glycyrrhetic acid is similar to that of cortisone. Glycyrrhetic acid derivatives are considered as bio-isosters of cortisone because both molecules are flat and similar at positions 3 and 11. This structural similarity might be the basis for licorice's anti-inflammatory action. Further, glycyrrhetic acid is known to inhibit both the 15-hydroxy-prostaglandin dehydrogenase and delta-13-prostaglandin dehydrogenase that metabolize the prostaglandins PGE-2 and PGF-2α to their respective inactive 15-keto-13,14-dihydro metabolites. Consequently, the level of prostaglandins in the gastrointestinal tract increases, stimulating pancreatic and mucous secretions in the intestines.

Thus, an anti-inflammatory and antiulcer an agent that combines both anti-inflammatory and antiulcer activities is desired.

SUMMARY

The glycyrrhetic acid derivatives can include:
2-(4-fluorobenzylidene)-3,11-dioxo-18β-olean-12-en-30-oic acid (2), having the structural formula:

2-(4-fluorobenzylidene)-3,11-dioxo-18β-olean[3,2-c]-1'H-5'-(4-fluorophenyl)-N-methylpyrazoline-12-en-30-oic acid (3), having the structural formula 2-(4-fluorobenzylidene)-3,11-dioxo-18β-olean[3,2-c]-1'H-5'-(4-fluorophenyl)-N-methylpyrazoline-12-en-30-oic acid (30→22β) lactone (4), having the structural formula or a pharmaceutically acceptable salt of Compounds (2), (3), or (4).

2-(4-fluorobenzylidene)-3,11-dioxo-18β-olean-12-en-30-oic acid (2) may be prepared by condensing 3-keto-glycyrrhetic acid (1) with 4-fluorobenzaldehyde. Treating 2-(4-fluorobenzylidene)-3,11-dioxo-18β-olean-12-en-30-oic acid (2) with N-methyl hydrazine in glacial acetic acid provides 2-(4-fluorobenzylidene)-3,11-dioxo-18β-olean[3,2-c]-1'-1-5β-(4-fluorophenyl)-N-methylpyrazoline-12-en-30-oic acid (3). Treating 2-(4-fluorobenzylidene)-3,11-dioxo-18β-olean[3,2-c]-1'-1-5β-(4-fluorophenyl)-N-methylpyrazoline-12-en-30-oic acid (3) with ethyl chloroformate and sodium azide in DMSO/THF provides 2-(4-fluorobenzylidene)-3,11-dioxo-18β-olean[3,2-c]-1'H-5'-(4-fluorophenyl)-N-methylpyrazoline-12-en-30-oic acid (30→22β) lactone (4).

The present compounds provide both anti-inflammatory and antiulcer effects.

These and other features of the present disclosure will become readily apparent upon further review of the following specification and drawings.

DETAILED DESCRIPTION OF THE PREFERRED EMBODIMENTS

Glycyrrhetic acid derivatives can include:
2-(4-fluorobenzylidene)-3,11-dioxo-18β-olean-12-en-30-oic acid (2), having the structural formula Compound (2)

2-(4-fluorobenzylidene)-3,11-dioxo-18β-olean[3,2-c]-1'H-5β-(4-fluorophenyl)-N-methylpyrazoline-12-en-30-oic acid (3), having the structural formula Compound (3)

2-(4-fluorobenzylidene)-3,11-dioxo-18β-olean[3,2-c]-1'H-5β-(4-fluorophenyl)-N-methylpyrazoline-12-en-30-oic acid (30→22β) lactone (4), having the structural formula Compound (4)

or a pharmaceutically acceptable salt of Compounds (2), (3), or (4).

Figure 1:
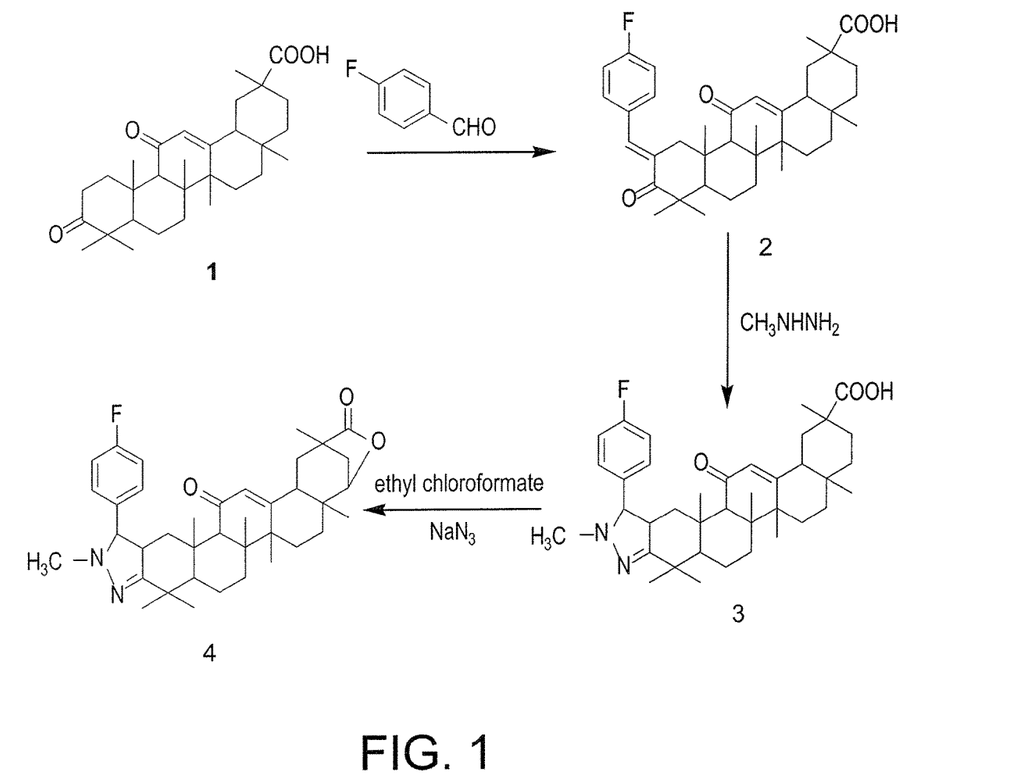
FIG. 1 is an exemplary reaction scheme for synthesis of the glycyrrhetic acid derivatives.

FIG. 1 depicts a reaction scheme by which exemplary glycyrrhetic acid derivatives can be prepared. As shown in FIG. 1, glycyrrhetic acid (1), i.e., 3-keto-glycyrrhetic, can be condensed with 4-fluorobenzaldehyde to afford 2-(4-fluorobenzylidene)-3,11-dioxo-18β-olean-12-en-30-oic acid (2). Treating 2-(4-fluorobenzylidene)-3,11-dioxo-18μ-olean-12-en-30-oic acid (2) with N-methyl hydrazine in glacial acetic acid provides 2-(4-fluorobenzylidene)-3,11-dioxo-18β-olean[3,2-c]-1'H-5'-(4-fluorophenyl)-N-methylpyrazoline-12-en-30-oic acid (3), which may in turn be treated with ethyl chloroformate and sodium azide in DMSO/THF to afford 2-(4-fluorobenzylidene)-3,11-dioxo-18β-olean[3,2-c]-1'H-5'-(4-fluorophenyl)-N-methylpyrazoline-12-en-30-oic acid (30→22β) lactone (4).

The glycyrrhetic acid derivatives can be used to treat inflammation and ulcers. As described in detail in the Examples below, each of compounds (2)-(4) exhibited potent anti-inflammatory and antiulcer activities when tested on animal models subjected to standard bioassays in comparison to reference pharmaceuticals and control conditions. The results of anti-inflammatory and antiulcer activity tests for each of compounds (2)-(4) are summarized in Examples 4-8, discussed below.

Each of compounds (2)-(4) showed potent anti-inflammatory and antiulcer activities, presumably, but non-limitingly, through proton pump inhibition. Anti-inflammatory activities appear to increase with increased similarity of the compounds to cortisone; these aspects of similarity include a flat cage and the presence of multi-carbonyl and olefin centers. The benzylidene moiety showed potent anti-inflammatory, presumably due to the flat nature of the enone and arylidene facilitating structural compatibility with COX-2 enzymes for inhibition. The pyrozoline moiety increases anti-inflammatory activities presumably by improved hydrogen bonding with COX-2 enzyme for inhibition. Finally, the five-member lactone moiety increases anti-inflammatory activities for similar structural reasons to the above, and in addition to improved binding to the COX-2 for inhibition. Improved antiulcer activities of the compounds (2)-(4) over previous compounds may be due to increased lipophilicity and improved structural compatibility with H+/K+-ATPase. Improved ability of compounds (3) and (4), in particular, to form Zwitterions and undergo hydrogen bonding increases antiulcer activity by facilitating approach to and bonding with H+/K+-ATPase. In the compound (4), both the pyrazoline and the sterically hindered five membered lactone form Zwitterions, and therefore, presumably is most effective at forming hydrogen bonds relative to the compounds (3) and (2), possibly leading to its greater antiulcer activity.

A pharmaceutically acceptable salt includes any non-toxic salt of the present anti-inflammatory and antiulcer compounds, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Also provided is a pharmaceutical composition including one or more glycyrrhetic acid derivatives. To prepare the pharmaceutical composition, one or more glycyrrhetic acid derivatives or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical composition can be administered to a patient in need thereof. The pharmaceutical composition can be administered by any conventional route of administration, including, but not limited to, intravenous, oral, subcutaneous, intramuscular, intradermal and parenteral. Depending on the route of administration, the anti-inflammatory and antiulcer compositions can be constituted into any form. For example, forms suitable for oral administration include solid forms, such as pills, gel caps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

The glycyrrhetic acid derivatives may be used as an anti-inflammatory agent and/or as an antiulcer agent. A therapeutically effective amount of the glycyrrhetic acid derivatives may be determined initially from in vivo assays described herein and adjusted for specific desired anti-inflammatory and antiulcer compositions using routine methods.

In the following Examples 1-3, all melting points are uncorrected and were measured using an electrothermal capillary melting point apparatus. IR spectra were recorded on a Shimadzu FT-IR 8101 PC infrared spectrophotometer. 1H-NMR spectra were determined with Bruker AM-200 MHz spectrometer. Chemical shifts are expressed on the δ (ppm) scale using TMS as the standard reference. Mass spectra were recorded on Finnigan SSQ operating at 70 eV. Elemental analysis was determined on a Perkin Elmer 240 (microanalysis), Microanalysis Center, Cairo University, Cairo, Egypt.

The following examples illustrate the present teachings.

Example 1

Synthesis of 2-(4-fluorobenzylidene)-3,11-dioxo-18β-olean-12-en-30-oic acid (2)

A solution of the compound having formula (1) (9.36 g, 20 mmol) and 4-fluorobenzaldehyde (20 mmol) in a mixture of ethanol (200 ml) and aqueous potassium hydroxide (10 ml, 30%) was made and stirred over night at room temperature. The separated solid product was crystallized from ethanol to give the compound having formula (2). Yield 98%, mp 233° C., $[\alpha]_D^{25}$=+69 (c 1, MeOH). IR (KBr, cm$^{-1}$): 3501 (OH), 3052 (CH, aromatic), 2981 (CH, aliphatic), 1746, 1730 (2C=O), 1654, 1644 (2C=C). $^1$H NMR (pyridine-d$_5$): d ppm 0.79 (s, β-3H, CH$_3$, C-28), 0.81 (s, α-3H, CH$_3$, C-23), 0.87 (d, α-1H, CH, C-5), 0.90 (s, β-3H, CH$_3$, C-24), 1.06 (s, β-3H, CH$_3$, C-25), 1.18 (s, β-3H, CH$_3$, C-26), 1.22 (m, α-H, CH, C-15), 1.26 (s, α-3H, CH$_3$, C-29), 1.27 (m, 13-1H, CH, C-21), 1.31 (s, α-3H, CH$_3$, C-29), 1.32 (m, β-1H, CH, C-19), 1.36 (m, β-1H, CH, C-7), 1.39 (m, β-1H, CH, C-6), 1.46 (m, α-1H, CH, C-21), 1.51 (t, α-1H, CH, C-9), 1.53 (m, α-1H, CH, C-7), 1.80 (m, α-1H, CH, C-19), 1.82 (m, α-1H, CH, C-22), 1.85 (m, α-1H, CH, C-6), 1.91 (m, 2H, CH$_2$, C-1), 1.96 (m, β-1H, CH, C-16), 2.04 (m, β-1H, CH, C-22), 2.12 (t, α-1H, CH, C-16), 2.19 (m, 13-H, CH, C-15), 3.30 (dd, β-1H, CH, C-18), 5.78 (s, 1H, CH, C-12), 7.30-7.45 (m, 4H, Ar—H), 6.71 (s, 1H, arylidene proton), 11.80 (s, 1H, OH, exchangeable with D$_2$O). $^{13}$C NMR (pyridine-d$_5$): d ppm 39.11 (C-1), 108.09 (C-2), 197.12 (C-3), 37.61 (C-4), 55.12 (C-5), 18.91 (C-6), 38.00 (C-7), 37.21 (C-8), 45.16 (C-9), 40.13 (C-10), 191.18 (C-11), 128.61 (C-12), 170.28 (C-13), 48.55 (C-14), 26.71 (C-15), 23.41 (C-16), 33.81 (C-17), 53.17 (C-18), 41.56 (C-19), 43.31 (C-20), 32.71 (C-21), 87.27 (C-22), 30.19 (C-23), 18.91 (C-24), 17.51 (C-25), 23.27 (C-26), 24.16 (C-27), 31.81 (C-28), 31.91 (C-29), 184.7 (C-30), 164.88 (C-arylidene), 122.92, 129.90, 115.66, 163.33 (6C, Ar—C). MS (EI): m/z 574 (100%) [M$^+$]. Anal. Calcd for C$_{37}$H$_{47}$FO$_3$ (574): Calcd C, 77.35; H, 8.18; F, 3.31. Found C, 77.30; H, 8.20; F, 3.30.

Example 2

Synthesis of 2-(4-fluorobenzylidene)-3,11-dioxo-18β-olean[3,2-c]-1'H-5'-(4-fluorophenyl)-N-methyl-pyrazoline-12-en-30-oic acid (3)

A mixture of (2) (5.74 g, 10 mmol) and methyl hydrazine (12 mmol), in glacial acetic acid (50 mL), was refluxed for 10 hours. After cooling, the separated solid product was filtered, then washed with cold water, dried and crystallized from the methyl acetate methanol to give compound (3). Yield 98%, mp 225° C., $[\alpha]_D^{25}$=+67 (c 1, MeOH). IR (KBr, 3508 (OH), 3048 (CH, aromatic), 2982 (CH, aliphatic), 1748 (C=O), 1654, (C=C); 1640, (C=N). $^1$H NMR (pyridine-d$_5$): d ppm 0.78 (s, β-3H, CH$_3$, C-28), 0.81 (s, α-3H, CH$_3$, C-23), 0.86 (d, α-1H, CH, C-5), 0.91 (s, β-3H, CH$_3$, C-24), 1.09 (s, β-3H, CH$_3$, C-25), 1.16 (s, β-3H, CH$_3$, C-26), 1.21 (m, α-H, CH, C-15), 1.25 (s, α-3H, CH$_3$, C-29), 1.26 (m, β-1H, CH, C-21), 1.29 (s, α-3H, CH$_3$, C-29), 1.32 (m, β-1H, CH, C-19), 1.35 (m, β-1H, CH, C-7), 1.41 (m, β-1H, CH, C-6), 1.47 (m, α-1H, CH, C-21), 1.51 (t, α-1H, CH, C-9), 1.58 (m, α-1H, CH, C-7), 1.79 (m, α-1H, CH, C-19), 1.80 (m, α-1H, CH, C-22), 1.85 (m, α-1H, CH, C-6), 1.90 (m, 2H, CH$_2$, C-1), 1.95 (m, β-1H, CH, C-16), 2.07 (m, β-1H, CH, C-22), 2.15 (t, α-1H, CH, C-16), 2.19 (s, 3H, NCH$_3$), 2.21 (m, β-H, CH, C-15), 2.40 (m, 1H, pyrazoline-H), 3.31 (dd, β-1H, CH, C-18), 3.40 (d, 1H, pyrazoline-H), 5.79 (s, 1H, CH, C-12), 7.31-7.48 (m, 4H, Ar—H), 11.80 (s, 1H, OH, exchangeable with D$_2$O). $^{13}$C NMR (pyridine-d$_5$): d ppm 39.12 (C-1), 28.29 (C-2), 163.40 (C-3), 37.64 (C-4), 55.15 (C-5), 18.95 (C-6), 38.20 (C-7), 37.23 (C-8), 45.16 (C-9), 40.15 (C-10), 191.22 (C-11), 128.62 (C-12), 170.23 (C-13), 48.53 (C-14), 26.71 (C-15), 23.44 (C-16), 33.85 (C-17), 53.15 (C-18), 41.56 (C-19), 43.36 (C-20), 32.77

(C-21), 87.28 (C-22), 30.14 (C-23), 18.94 (C-24), 17.55 (C-25), 23.26 (C-26), 24.17 (C-27), 31.87 (C-28), 31.91 (C-29), 184.7 (C-30), 164.91 (C-arylidene), 122.91, 129.91, 115.62, 163.33 (6C, Ar—C), 29.38 (NCH$_3$-Pyrazoline), 64.61 (C-5, Pyrazoline). MS (EI): m/z 602 (100%) [M$^+$]. Anal. Calcd for C$_{38}$H$_{51}$FN$_2$O$_3$ (602): Calcd C, 77.74; H, 8.47; F, 3.15; N, 4.65. Found C, 77.72; H, 8.48; F, 3.14; N, 4.65.

Example 3

Synthesis of 2-(4-fluorobenzylidene)-3,11-dioxo-18β-olean[3,2-c]-1'H-5'-(4-fluorophenyl)-N-methyl-pyrazoline-12-en-30-oic acid (30→22β) lactone (4)

A mixture of compound 3 (6.02 gm, 10 mmol) and ethyl chloroformate (1.25 ml, 10 mmol) in a mixture of tetrahydrofuran and dimethylsulfoxide (125 ml, 1:1) was stirred for one hour in the presence of trimethylamine (0.75 ml, 10 mmol). Sodium azide (0.65 gm, 10 mmol) was added to the previous solution and the resulting solution was stirred for another one hour. The reaction mixture was poured into water to obtain a precipitate; the obtained precipitate was filtered off, dried and washed with benzene to remove un-reacted starting material. The obtained solid product was crystallized from dry benzene to give the corresponding lactone derivative (4). Yield 88%, mp 309° C., $[\alpha]_D^{25}$=+80 (c 1, MeOH). IR (KBr, cm$^{-1}$): 3049 (CH, aromatic), 2986 (CH, aliphatic), 1747 (C=O), 1655, (C=C); 1641, (C=N). $^1$H NMR (pyridine-d$_5$): d ppm 0.76 (s, β-3H, CH$_3$, C-28), 0.79 (s, α-3H, CH$_3$, C-23), 0.83 (d, α-1H, CH, C-5), 0.88 (s, 3-3H, CH$_3$, C-24), 1.01 (s, β-3H, CH$_3$, C-25), 1.11 (s, 3-3H, CH$_3$, C-26), 1.17 (m, α-H, CH, C-15), 1.21 (s, α-3H, CH$_3$, C-29), 1.25 (m, β-1H, CH, C-21), 1.28 (s, α-3H, CH$_3$, C-29), 1.31 (m, β-1H, CH, C-19), 1.36 (m, β-1H, CH, C-7), 1.42 (m, β-1H, CH, C-6), 1.48 (m, α-1H, CH, C-21), 1.52 (t, α-1H, CH, C-9), 1.57 (m, α-1H, CH, C-7), 1.77 (m, α-1H, CH, C-19), 1.84 (m, α-1H, CH, C-6), 1.91 (m, 2H, CH$_2$, C-1), 1.95 (m, β-1H, CH, C-16), 2.11 (t, α-1H, CH, C-16), 2.16 (s, 3H, NCH$_3$), 2.21 (m, β-H, CH, C-15), 2.39 (m, 1H, pyrazoline-H), 3.30 (dd, β-1H, CH, C-18), 3.41 (d, 1H, pyrazoline-H), 4.28 (m, eq-1H, CH, C-22), 5.75 (s, 1H, CH, C-12), 7.311-7.51 (m, 4H, Ar—H). $^{13}$C NMR (pyridine-d$_5$): d ppm 39.23 (C-1), 28.43 (C-2), 163.43 (C-3), 37.64 (C-4), 55.13 (C-5), 18.95 (C-6), 38.32 (C-7), 37.34 (C-8), 45.56 (C-9), 40.13 (C-10), 191.24 (C-11), 128.63 (C-12), 170.24 (C-13), 48.55 (C-14), 26.76 (C-15), 23.47 (C-16), 33.85 (C-17), 53.34 (C-18), 41.57 (C-19), 43.64 (C-20), 32.56 (C-21), 65.26 (C-22), 30.13 (C-23), 18.90 (C-24), 17.50 (C-25), 23.20 (C-26), 24.14 (C-27), 31.84 (C-28), 31.92 (C-29), 183.77 (C-30), 164.92 (C-arylidene), 122.92, 129.94, 115.66, 163.37 (6C, Ar—C), 29.38 (NCH$_3$-Pyrazoline), 64.68 (C-5, Pyrazoline). MS (EI): m/z 600 (100%) [M$^+$]. Anal. Calcd for C$_{38}$H$_{49}$FN$_2$O$_3$ (602): Calcd C, 76.00; H, 8.16; F, 3.16; N, 4.16. Found C, 76.00; H, 8.15; F, 3.15; N, 4.15.

Example 4

Cotton Pellet-Induced Granuloma Bioassay

An animal model cotton pellet-induced granuloma bioassay was used to determine ED$_{50}$ for the compounds (2)-(4). Adult male Sprague Dawley rats (120-140 g), were used in the cotton pellet-induced granuloma bioassays. The rats were acclimated one week prior to use and allowed unlimited access to standard rat chow and water. Prior to the start of the experiment, the animals were randomly divided into groups of six rats each. Cotton pellet (35±1 mg) cut from dental rolls were impregnated with 0.2 ml (containing 0.01 mmol) of a solution of each of compounds (2)-(4) in chloroform, and the solvent was allowed to evaporate. Each cotton pellet was subsequently injected with 0.2 ml of an aqueous solution of antibiotics (1 mg penicillin G and 1.3 mg dihydrostreptomycin/ml). Two pellets were implanted subcutaneously, one in each axilla of the rat, under mild general anesthesia. One group of animals received the standard reference pharmaceutical indomethacin and the antibiotics at the same level. Pellets containing only the antibiotics were similarly implanted in control rats. Seven days later, the animals were sacrificed and the two cotton pellets, with adhering granulomas, were removed, dried for 48 h at 60° C. and weighed. The increment in dry weight (difference between the initial and final weight) was taken as a measure of the dry weight of granuloma±SEM. The dry weight of granuloma and the percentage reduction in dry weight of granuloma relative to the respective control value were calculated for all rats. The ED$_{50}$ values were determined through dose response curves using doses of 4, 7, 10 and 15 µmol for each compound.

Figure 2:
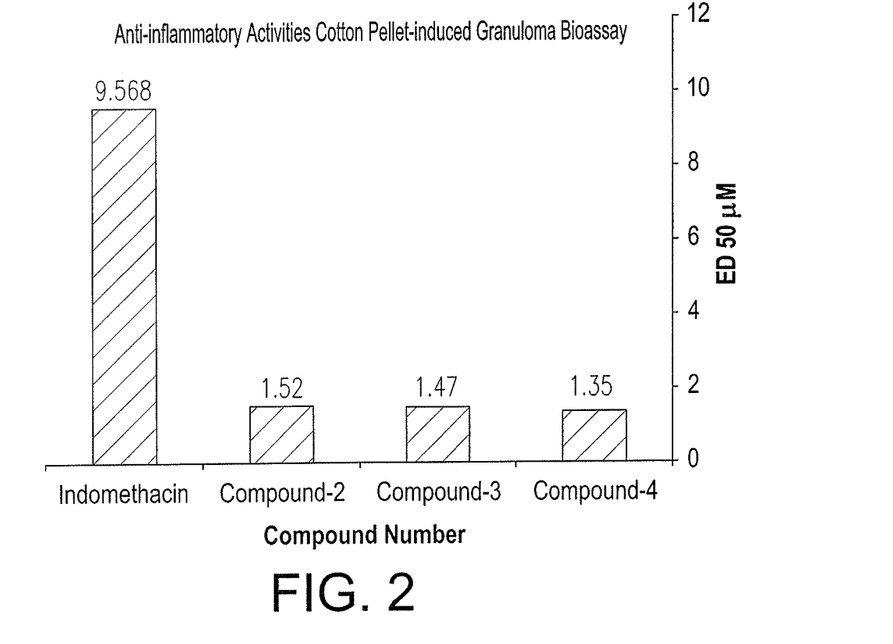
FIG. 2 is a graph showing the anti-inflammatory activities of the glycyrrhetic acid derivatives.

The ED$_{50}$ for compounds (2)-(4) were 1.52, 1.47 and 1.35 mol, respectively. Each of compounds (2)-(4) demonstrated more anti-inflammatory activity than control compound, indomethacin (ED$_{50}$ 9.568 µmol) (FIG. 2 and Table 1).

TABLE 1

| The anti-inflammatory activity (ED$_{50}$, mmol) | |
|---|---|
| Test compound | ED$_{50}$ (µmol) |
| 2 | 1.52 ± 0.0019 |
| 3 | 1.47 ± 0.0021 |
| 4 | 1.35 ± 0.0034 |
| Indomethacin | 9.568 ± 0.098 |

All data in Table 1 is significantly different from control (P < 0.001).

Example 5

Carrageenan-Induced Rat Paw Edema

Male albino rats weighing 120-150 g were used in these experiments. The rats were kept in an animal house under standard conditions of light and temperature with free access to food and water. The animals were randomly divided into groups of six rats each for each experimental and control group. The paw edema was induced by subplantar injection of 50 ml of 2% carrageenan solution in saline (0.9%). Indomethacin and each of compounds (2)-(4) were dissolved in DMSO and injected subcutaneously at a dose of 10 µmol/kg body weight 1 h prior to carrageenan injection. A control group was injected with DMSO only. The volume of paw edema (ml) was determined by means of a plethysmometer immediately after carrageenan injection and 4 h later. The increase in paw volume between 0 h and 4 h after carrageenan injection was measured [7]. The percentage protection against inflammation was calculated according to the following formula: % Protection=100%×(Vc−Vd)/Vc where Vc is the 4 h increase in paw volume in the control animals (control) and Vd is the 4 h increase in paw volume in the test animals.

Data are expressed as the mean±SEM. Significant difference between the control and test groups was determined using Student's t-test and P values. The difference in results was considered significant when P<0.001. The anti-inflammatory activity of each of compounds (2)-(4) relative to that of indomethacin was also calculated.

As shown in Table 2 below, the carrageenan-induced rat paw edema revealed that the percentage of protection against paw edema for compounds (2)-(4) and indomethacin were 98.40, 98.49, 98.77 and 74.49, respectively. Each of compounds (2)-(4) demonstrated much more reactivity than indomethacin; the relative activities of each of the compounds (2)-(4) to indomethacin were 132.09, 132.21 and 132.58, respectively.

TABLE 2

Effects of compounds (2)-(4) on Carrageenan-induced rat paw edema (ml), percent-age protection and activity relative to indomethacin

| Test compound | Increase in paw edema (ml) ± SEM[a,b] | % Protection | Activity relative to indomethacin |
|---|---|---|---|
| Control | 0.988 ± 0.0006 | 0 | 0 |
| Indomethacin | 0.25 ± 0.0005 | 74.49 | 100 |
| 2 | 0.0157 ± 0.0004 | 98.40 | 132.09 |
| 3 | 0.0148 ± 0.0003 | 98.49 | 132.21 |
| 4 | 0.0121 ± 0.0002 | 98.77 | 132.58 |

[a]SEM denotes the standard error of the mean.
[b]All data are significantly different from control (P < 0.001).

Example 6

Human COX-1 and COX-2 Enzymatic Assay

Human COX-1 and COX-2 enzymatic assays were used to determine the selectivity of each of compounds (2)-(4) towards inhibition of both COX-2 and COX-1.

Human COX-1 and COX-2 activities were determined as described by Wakitani et al. 0.2 ml of 100 mmol Tris HCl buffer (pH 8) containing hematin (2 mmol) and tryptophan (5 mmol) as cofactors. The reaction mixture was pre-incubated with each test compound individually for 5 min at 24° C. [14C]-arachidonic acid (100.00 dpm, 30 mmol) was added to the mixture and then incubated for 2 min (for COX-1) or 45 min (for COX-2) at 24° C. The reaction was stopped by the addition of 400 μl of a solution composed of $Et_2O$/MeOH/1 M citric acid (30:4:1, v/v/v). After centrifugation of the mixture at 1700×/g for 5 min at 4° C., 50 μl of the upper phase was applied to a thin layer chromatography plate. Thin layer chromatography was performed at 4° C. with solvent system of $Et_2O$/MeOH/AcOH (90:2:0.1, v/v/v). Enzyme activity was calculated from the percent conversion of arachidonic acid to PGH2 and its de-composition products, using radiometric photographic system. The concentration of the compound causing 50% inhibition ($IC_{50}$) was calculated.

Figure 4:
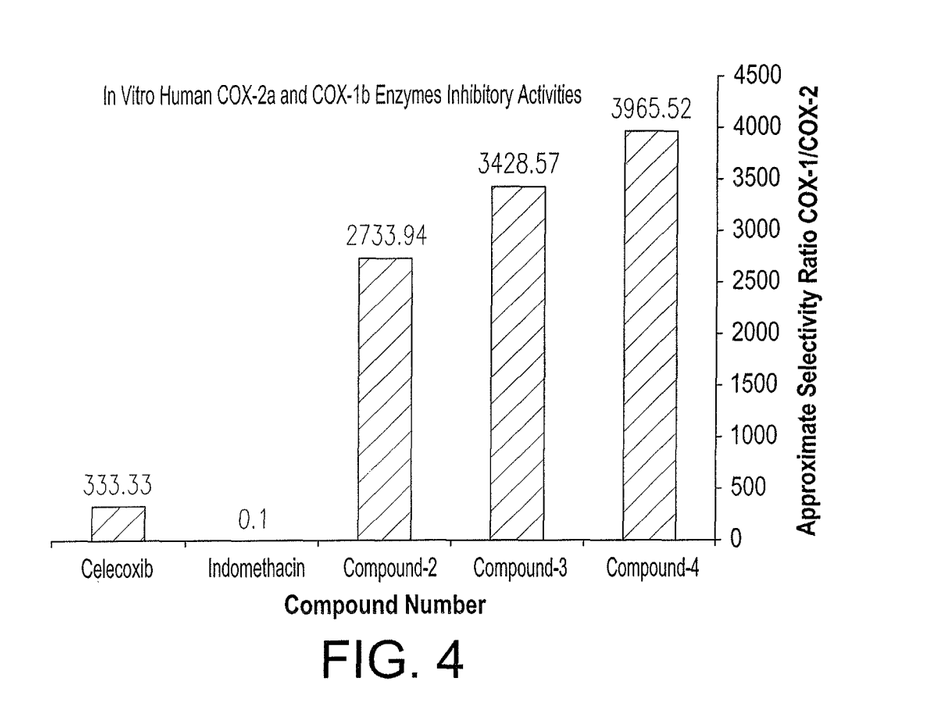
FIG. 4 is a graph showing COX-2a and COX-1b enzyme inhibitory activities of the glycyrrhetic acid derivatives.

As reflected in FIG. 4 and Table 3, each of compounds (2)-(4) showed great selectivity to inhibit COX-2 relative to COX-1. The selectivity ratio COX-1/COX-2 for each of compounds (2)-(4) were 2733.94, 3438.57 and 3965.52, respectively. Each of compounds (2)-(4) showed greater selectivity in inhibiting COX-2 relative to COX-1 compared to control COX-2 inhibitor, Celecoxib (COX-1/COX-2 ratio of 333.33).

TABLE 3

In Vitro Human COX-2a and COX-1b enzyme inhibitory activities of compounds (2)-(4)

| Test compound | COX-2 $IC_{50}$ (μmol) | COX-1 $IC_{50}$ (μmol) | Approximate selectivity ratio COX-1/COX-2 |
|---|---|---|---|
| Indomethacin | 2.63 | 0.26 | 0.10 |
| Celecoxib | 0.3 | 100 | 333.33 |
| 2 | 0.109 | 298 | 2733.94 |
| 3 | 0.091 | 312 | 3428.57 |
| 4 | 0.087 | 345 | 3965.52 |

All data are significantly different from control (P < 0.001).

Example 7

Acute Toxicity

The oral acute toxicity of compounds was investigated using male mice (20 g each) according to previously reported methods [9]. The animals were divided into groups of six mice each. The compounds were given orally, suspended in 1% gum acacia, in doses of 1, 10, 100, 200, 250, 300 mg/kg.

The mortality percentage in each group was recorded after 24 h.

Additionally, the test compounds were investigated for their parenteral acute toxicity in groups of six mice each as reported earlier [10]. The compounds, or their vehicle propylene glycol (control), were given by intraperitoneal injection in doses of 10, 25, 50, 75, 100 mg/kg. The percentage survival was followed up to seven days.

Each of compounds (2)-(4) showed high safety and wide therapeutic windows, with $LD_{50}$ measured to be 3100.11, 3356.78 and 3456.78, respectively.

TABLE 4

Acute toxicity of each of compounds (2)-(4)

| Test compounds | $LD_{50}$ mg/kg |
|---|---|
| 2 | 3100.11 |
| 3 | 3356.78 |
| 4 | 3456.78 |

Example 8

Antiulcer Activities

Pyloric ligation ulcer models were used to test each of compounds (2)-(4) for antiulcer activity. Male rats (140 and 175 g) were selected for pyloric ligation ulcer model experiments and divided into eleven groups consisting of six animals each. The rats were fasted overnight. One group received normal saline 2 ml/kg (negative control), the second group received omeprazole 40 mg/kg (positive control) and the other groups received each of the compounds (2)-(4) (100 mg/kg) by oral route 30 min prior to pyloric ligation. Animals were sacrificed 4 h later and their stomachs were opened to collect the gastric contents. The gastric contents were centrifuged at 1000 rpm for 10 min. One ml of the supernatant liquid was pipetted out and diluted to a total volume of 10 ml with distilled water. The solution was titrated against 0.01 N sodium hydroxide solution using Topfer's reagent to indicate the end point when the solution turned orange. The volume of NaOH consumed was taken as corresponding to the free acidity. Titration was further continued until the solution regained pink color. The volume of sodium hydroxide solution required to achieve the pink color was noted and total acidity calculated. After opening the stomach, the ulcer index was calculated.

The results are expressed as mean±SEM. The difference between groups was determined using the one way analysis of variance (ANOVA) followed by Dunnett's test. P<0.05 was considered significant.

Each of compounds (2)-(4) exhibited potent antiulcer activity, greatly decreasing the ulcer index compared to standard antiulcer agent Ompeprazole.

The ulcer index of each of compounds (2)-(4) and Omeprazole were measured to be 1.16, 1.12, 1.04 and 3.31, respectively.

Figure 5:
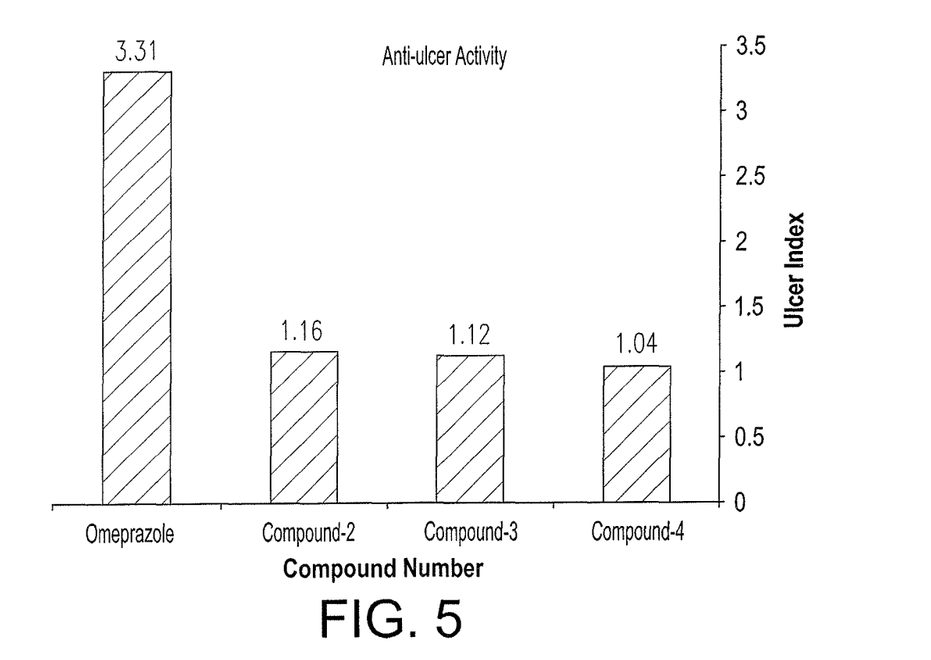
FIG. 5 is a graph showing anti-ulcer activities of the glycyrrhetic acid derivatives.

Each of compounds (2)-(4) reduced both free acid and total acid to large extent relative to Omeprazole, in increasing order of potency (FIG. 5 and Table 5).

TABLE 5

Antiulcer activity

| Comp. No. | Ulcer Index | Free acid mEq/L | Total acid mEq/L |
|---|---|---|---|
| Control | | 3.28 | 11.14 |
| Omeprazole | 3.31 | 0.43 | 0.33 |
| 2 | 1.16 | 0.09 | 0.09 |
| 3 | 1.12 | 0.08 | 0.08 |
| 4 | 1.04 | 0.06 | 0.06 |

Values were calculated as the mean value of data from three separate experiments.
All results are significantly different from control values (P ≤ 0.005).
All results are significant different from reference standard values (P ≤ 0.005).

Example 9

Human, Rat, and Dog Microsomal COX Assays

Whole kidneys (1-10 g of tissue) were suspended in 50 mM potassium phosphate buffer, pH 7.1, containing 0.1 M NaCl, 2 mM EDTA, and 1 mM phenylmethylsulfonyl fluoride (homogenization buffer). Samples were then homogenized for 2 min on ice using a hand-held tissue homogenizer (Biospec Products, Inc., Bartlesville, Okla.) at maximum setting, after which they were sonicated for 10 s using a microultrasonic cell disrupter (Kontes, Vineland, N.J.). Tissue homogenates were then centrifuged at 100,000 g for 1 h at 4° C. The 100,000 g microsomal pellet was resuspended in homogenization buffer and was sonicated (2 3 10 s) on ice. The resulting human, rat, and dog kidney microsomal suspensions were diluted to protein concentrations of approximately 6, 10, and 12 mg/ml, respectively. Aliquots of microsomal preparations were stored at 280° C. and thawed on ice immediately before assays.

Rofecoxib was preincubated at room temperature for 5 or 15 min with a microsomal preparation from rat, dog, or human kidneys. The preincubation buffer contained 0.1 M Tris HCl, pH 7.4, 10 mM EDTA, 0.5 mM phenol, 1 mM reduced glutathione, 1 mM hematin, and a protein concentration of 0.12 mg/ml. Arachidonic acid was then added to a final concentration of 2 mM, and the samples were further incubated at room temperature for 40 min. After the incubation period, the reaction was terminated by the addition of 25 ml of 1 N HCl with mixing. Samples were neutralized by the addition of 25 ml of 1 N NaOH before analysis of the amount PGE2 by radioimmunoassay.

Assays were performed in duplicate or triplicate. Control reaction mixtures contained ethanol vehicle instead of arachidonic acid. In the absence of the addition of arachidonic acid, levels of PGE2 in samples from human, dog, and rat kidney microsomes were approximately 1.5 ng/mg protein, 0.1 ng/mg protein, and 6.7 ng/mg protein, respectively. In the presence of arachidonic acid, levels of PGE2 in these preparations increased to approximately 4.2 ng/mg protein, 1.2 ng/mg protein, and 22 ng/mg protein, respectively. COX activity in the absence of test compounds is defined as the difference between PGE2 levels in samples incubated in the presence of arachidonic acid or ethanol vehicle.

Example 10

H+/K+-ATPase (Proton Pump) Inhibition

Membrane vesicles containing $H^+/K^+$-ATPase were prepared from pig stomachs obtained from a local slaughter house. Pigs were fasted overnight before slaughter. The gastric mucosa of four stomachs was rinsed with cold saturated NaCl solution for 3-5 min. The superficial cells, cell debris plus the mucus were wiped off with the edge of a plastic ruler and paper towels. The mucosa was scraped off. About 100 g of scrapings were divided into portions of 10 g and homogenized in 0.25 M sucrose with seven strokes in a Potter-Elvehjem Teflon-glass homogenizer. The total volume was 600 ml, which was centrifuged at 20,000 g for 40 min. The pellet was discarded. The supernatant was centrifuged at 75,000 g for 1 h. The resulting microsomal pellet was homogenized in 30 ml 0.25 M sucrose. Aliquots of 15 ml were transferred to 100 ml centrifuge tubes and layered on top of step gradients, from the bottom comprising 25 ml 37% sucrose (w/v) and 45 ml 7.5% Ficoll (w/v) in 0.25 M sucrose. The tubes were centrifuged at 75,000 g for 1 h in a 6×100 ml ME angle rotor at 4° C. The gradient was then fractionated by pumping Fluoroinert 70 through narrow tubing in a fractionating cap down to the bottom of the tube. Fractions are collected from top through a center hole in the fractionating cap. The yield of vesicles in a typical preparation is about 50-75 mg protein. In order to maintain a stable vesicular structure for a long period of time, the vesicles were frozen at −70° C. under nitrogen, and could then be kept for several months without decrease of $H^+/K^+$-ATPase activity.

The ATPase activity was measured at 37° C. as the release of inorganic phosphate (Pi) from ATP. The test drug and the standard (omeprazole) are pre-incubated in concentrations of 0.01 to 100.0 µM in enzyme containing buffers in parallel at pH 6.0 and 7.4 for 30 min at 37° C. Then, the medium of pH 6.0 is adjusted with HEPES/Tris buffer to pH 7.4. The enzyme reaction is started by addition of nigericin and Tris/ATP. The total reaction volume is 1 ml, containing 20 µg vesicular protein, 4 mM $MgCl_2$, 10 mM KCl, 20 µM nigericin, 2 mM Tris-ATP, 10 mM HEPES and additionally 2 mM Pipes for the pre-incubation medium at pH 6.0. After 4 mM at 37° C., the reaction is stopped by the addition of 10 ml of 50% trichloroacetic acid. The denatured protein was spun down and the Pi content is determined according to Le Bel et al. (1978) [11] and based on the reduction of a phosphomolybdate complex by p-methyl-aminophenol sulfate in a copper acetate buffer or according to Carter and Karl (1982) [12] based on the reaction of phosphomolybdate with the basic dye malachite green.

$IC_{50}$ values were calculated by probit analysis, whereby 0% corresponds to 4 mM $Mg^{2+}$-dependent and 100% to 4 mM $Mg^{2+}$ plus 10 mM $K^+$-dependent ATP hydrolysis. $IC_{50}$ values of the test compound at different pH values were compared with $IC_{50}$ values of the standard. Statistical differences (P<0.05) were calculated by Student's t-test.

Figure 3:
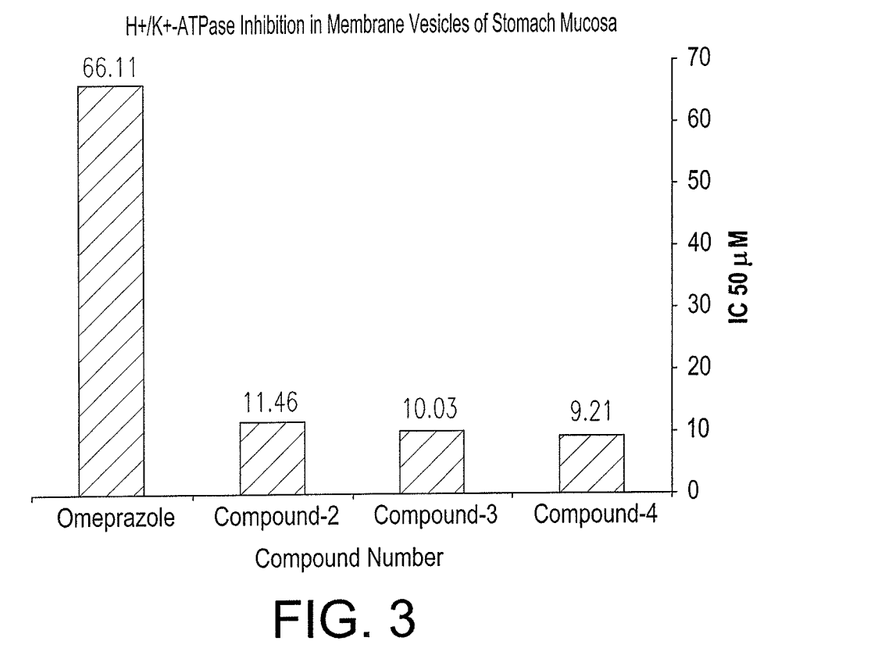
FIG. 3 is a graph showing H+/K+ATPase inhibition in membrane vesicles of stomach mucosa of the glycyrrhetic acid derivatives.

The mechanism of antiulcerogenic activity of the compounds (2)-(4) appears to be via versatile proton pump inhibitor activity, as confirmed by their exhibited $H^+/K^+$-ATPase inhibition in membrane vesicles of stomach mucosa (FIG. 3 and Table 6).

TABLE 6

$H^+/K^+$-ATPase inhibition in membrane vesicles of stomach mucosa

| Comp. No. | $IC_{50}$ μM |
| --- | --- |
| Omeprazole | 66.11 ± 1.11 |
| 2 | 11.46 ± 0.0090 |
| 3 | 10.03 ± 0.0072 |
| 4 | 9.21 ± 0.0076 |

Values were calculated as the mean value of data from three separate experiments.
All results are significantly different from control values (P ≤ 0.005).
All results are significant different from reference standard values (P ≤ 0.005).

It is to be understood that the anti-inflammatory and antiulcer composition of the present application is not limited to the specific embodiments described above, but encompasses any and all embodiments within the scope of the generic language of the following claims enabled by the embodiments described herein, or otherwise shown in the drawing or described above in terms sufficient to enable one of ordinary skill in the art to make and use the claimed subject matter.

We claim:

1. A glycyrrhetic acid derivative, comprising a compound, having the structural formula:

(2)

or a pharmaceutically acceptable salt thereof.

2. A pharmaceutical composition, comprising the compound of claim 1 and a pharmaceutically acceptable carrier.

3. A method of treating an ulcer, comprising administering to a patient in need thereof a therapeutically effective amount of the compound of claim 1.

4. A method of treating inflammation, comprising administering to a patient in need thereof a therapeutically effective amount of the compound of claim 1.

5. A method of synthesizing the compound of claim 1, comprising:
condensing 3-keto-glycyrrhetic acid with 4-fluorobenzaldehyde to provide the compound of claim 1.

6. A glycyrrhetic acid derivative, comprising a compound having the structural formula:

(3)

or a pharmaceutically acceptable salt thereof.

7. A pharmaceutical composition, comprising the compound of claim 6 and a pharmaceutically acceptable carrier.

8. A method of treating an ulcer, comprising administering to a patient in need thereof a therapeutically effective amount of the compound of claim 6.

9. A method of treating inflammation, comprising administering to a patient in need thereof a therapeutically effective amount of the compound of claim 6.

10. A method of synthesizing the compound of claim 6, comprising:
condensing 3-keto-glycyrrhetic acid (1) with 4-fluorobenzaldehyde to provide 2-(4-fluorobenzylidene)-3,11-dioxo-18β-olean-12-en-30-oic acid (2), having the structural formula (2)

treating 2-(4-fluorobenzylidene)-3,11-dioxo-18β-olean-12-en-30-oic acid (2) with N-methyl hydrazine in glacial acetic acid to provide the compound of claim 6.

11. A glycyrrhetic acid derivative, comprising a compound having the structural formula:

(4)

or a pharmaceutically acceptable salt thereof.

12. A pharmaceutical composition, comprising the compound of claim 11 and a pharmaceutically acceptable carrier.

13. A method of treating an ulcer, comprising administering to a patient in need thereof a therapeutically effective amount of the compound of claim 11.

14. A method of treating inflammation, comprising administering to a patient in need thereof a therapeutically effective amount of the compound of claim 11.

15. A method of synthesizing the compound of claim 11, comprising:

condensing 3-keto-glycyrrhetic acid (1) with 4-fluorobenzaldehyde to provide 2-(4-fluorobenzylidene)-3,11-dioxo-18β-olean-12-en-30-oic acid (2), having the structural formula (2)

treating 2-(4-fluorobenzylidene)-3,11-dioxo-18β-olean-12-en-30-oic acid (2) with N-methyl hydrazine in glacial acetic acid to provide 2-(4-fluorobenzylidene)-3,11-dioxo-18β-olean[3,2-c]-1'H-5'-(4-fluorophenyl)-N-methylpyrazoline-12-en-30-oic acid (3), having the structural formula (3)

treating 2-(4-fluorobenzylidene)-3,11-dioxo-18β-olean[3,2-c]-1'H-5'-(4-fluorophenyl)-N-methylpyrazoline-12-en-30-oic acid (3) with ethyl chloroformate and sodium azide to provide the Compound of claim 11.

\* \* \* \* \*